US012341227B2

(12) United States Patent
Yandrasits et al.

(10) Patent No.: US 12,341,227 B2
(45) Date of Patent: Jun. 24, 2025

(54) PERFLUOROSULFONYL MONOMERS SUITABLE FOR FLUOROPOLYMERS AND FUEL CELL MEMBRANE ARTICLES

(71) Applicant: 3M INNOVATIVE PROPERTIES COMPANY, St. Paul, MN (US)

(72) Inventors: Michael A. Yandrasits, Hastings, MN (US); Miguel A. Guerra, Woodbury, MN (US); Carl A. Laskowski, Minneapolis, MN (US); Matthew J. Lindell, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 575 days.

(21) Appl. No.: 17/739,227

(22) Filed: May 9, 2022

(65) Prior Publication Data

US 2023/0006230 A1    Jan. 5, 2023

Related U.S. Application Data

(60) Provisional application No. 63/196,729, filed on Jun. 4, 2021.

(51) Int. Cl.
*H01M 8/1032* (2016.01)
*C07C 309/82* (2006.01)
*C08F 214/26* (2006.01)
*C08F 216/14* (2006.01)
*H01M 8/10* (2016.01)
*H01M 8/1004* (2016.01)
*H01M 8/1039* (2016.01)

(52) U.S. Cl.
CPC ......... *H01M 8/1032* (2013.01); *C07C 309/82* (2013.01); *C08F 214/262* (2013.01); *C08F 216/1475* (2020.02); *H01M 8/1004* (2013.01); *H01M 8/1039* (2013.01); *H01M 2008/1095* (2013.01); *H01M 2300/0082* (2013.01)

(58) Field of Classification Search
CPC ............ H01M 8/1032; H01M 8/1004; H01M 8/1039; H01M 2008/1095; H01M 2300/0082; H01M 8/1058; H01M 4/621; H01M 50/409; C07C 309/82; C08F 214/262; C08F 216/1475; Y02E 60/50
See application file for complete search history.

(56) References Cited

U.S. PATENT DOCUMENTS

| 2,732,398 A |   | 1/1956  | Brice |
|---|---|---|---|
| 4,348,310 A | * | 9/1982  | Silva ............... C08J 5/2237 524/544 |
| 4,425,199 A |   | 1/1984  | Hamada et al. |
| 5,599,614 A |   | 2/1997  | Bahar et al. |
| 6,624,328 B1 |   | 9/2003  | Guerra et al. |
| 6,703,533 B1 |   | 3/2004  | Belen'Kii et al. |
| 7,129,298 B2 |   | 10/2006 | Ono et al. |
| 7,348,088 B2 |   | 3/2008  | Hamrock et al. |
| 7,575,534 B2 |   | 8/2009  | Gleasman et al. |
| 8,367,267 B2 |   | 2/2013  | Frey et al. |
| 8,628,871 B2 |   | 1/2014  | Frey et al. |
| 9,023,496 B2 |   | 5/2015  | Pierpont et al. |
| 2004/0107869 A1 |   | 6/2004  | Velamakanni et al. |
| 2004/0236047 A1 |   | 11/2004 | Ono et al. |
| 2013/0101918 A1 |   | 4/2013  | Yandrasits et al. |

FOREIGN PATENT DOCUMENTS

| CN | 101733014 | * | 6/2010 | ............ B01D 71/32 |
|---|---|---|---|---|
| EP | 1306407 A1 |   | 5/2003 | |
| JP | 6026145 B2 |   | 6/1985 | |
| JP | 2002047315 A2 |   | 2/2002 | |
| WO | 2002012392 A1 |   | 2/2002 | |
| WO | 2017053563 A1 |   | 3/2017 | |

OTHER PUBLICATIONS

Scifinder search (Year: 2025).*
STIC Search (Year: 2025).*
"Open Circuit Voltage (OCV) Test", A US DOE Accelerated Test Method, The United States Department of Energy, Hydrogen and Fuel Cell Technologies Office Multi-Year Research, Development and Demonstration Plan 2017 Section 3.4, 58 pages.
Burgess, Synthetic access to an elusive high-temperature perfluoroisopropenyl ether prepolymer for radical copolymerization, Chemical Communications, 2018, vol. 54, No. 74, pp. 10439-10442.
Coms, "The Chemistry of Fuel Cell Membrane Chemical Degradation", ECS Transactions, 2008, vol. 16 No. 2, pp. 235-255.
Cooper, "Progress Toward Accurate Through-Plane Ion Transport Progress Toward Accurate Through-Plane Ion Transport", Journal of The Electrochemical Society, Jan. 2010, Vo. 157, No. 11, pp. B1731-B1739.
Danilczuk, "In-Depth Profiling of Degradation Processes in a Fuel Cell: 2D Spectral-Spatial FTIR Spectra of Nafion Membranes", ACS Macro Letters, Feb. 2012, vol. 1, No. 2, pp. 280-285.

(Continued)

*Primary Examiner* — Helen Oi K Conley
(74) *Attorney, Agent, or Firm* — Carolyn A. Fischer

(57) ABSTRACT

Presently described is a monomer having the formula:

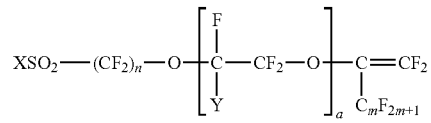

wherein
n ranges from 2 to 8;
Y is F or $C_mF_{2m+1}$;
a is 0, or averages 1 to 2;
m is independently 1, 2, 3, or 4; and
X is F or OH.
Also described is a method of making such monomer, various compounds prepared during while making the monomer, fluoropolymers comprising polymerized units of such monomer, fuel cell membranes, membrane electrode assemblies, and methods of making fluoropolymers.

14 Claims, No Drawings

(56) References Cited

OTHER PUBLICATIONS

Hill, "Octafluoroisobutylene Epoxide Derivatives", Journal of Fluorine Chemistry, Feb. 1977, vol. 9, No. 2, pp. 97-112.
Howell, "The preparation of primary poly-hexafluoropropylene oxide halides (poly-HFPO-CF2X where X ¼ I, Br, Cl and F)", Journal of Fluorine Chemistry, Oct. 2004, vol. 125, No. 10, pp. 1513-1518.
Knunyants, "Cleavage of Perfluoroisobutylene Oxide By Perfluoroalkoxy Anions", Bulletin of the Academy of Sciences of the USSR, Division of Chemical Science, May 1972, vol. 21, pp. 1085-1088. (Translated from Izvestiya Akademii Nauk SSSR, Seriya Khimicheskaya, No. 5, pp. 1133-1137, May 1972).
Schoemaker, "Evaluation of Hydrogen Crossover through Fuel Cell Membranes", Fuel Cells, Jun. 2014, vol. 14, No. 3, pp. 412-415.
Yandrasits, "Liquid Chromatography Mass Spectrometry Analysis of Effluent Water from PFSA Membrane Fuel Cells Operated at OCV", Journal of The Electrochemical Society, Feb. 2021, vol. 168 (024517), 17 pages.
Yu, "Mechanism for Degradation of Nafion in PEM Fuel Cells from Quantum Mechanics Calculations", Journal of the American Chemical Society, Dec. 2011, vol. 133, No. 49, pp. 19857-19863.

\* cited by examiner

PERFLUOROSULFONYL MONOMERS SUITABLE FOR FLUOROPOLYMERS AND FUEL CELL MEMBRANE ARTICLES

This invention was made with Government support under Cooperative Agreement DE-EE0009244 awarded by DOE. The Government has certain rights in this invention.

SUMMARY

Presently described is a monomer having the formula:

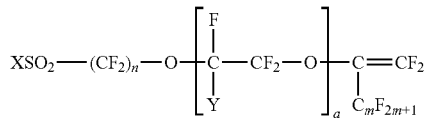

wherein
n ranges from 2 to 8;
Y is F or $C_mF_{2m+1}$;
a is 0, or averages 1 to 2;
m is independently 1, 2, 3, or 4; and
X is F or OH.

Fluoropolymers prepared from such monomers can advantageously have improved durability due to the energy barrier to abstract a fluorine atom by a hydrogen atom (H·) from the $C_mF_{2m+1}$ of the ethylenically unsaturated group is greater than the energy barrier to abstract a tertiary fluorine, i.e. a fluorine atom of $C_mF_{2m+1}$, wherein m is 0.

Also described is a method of making such monomer.

In other embodiments, various compounds are described. Some representative compounds include

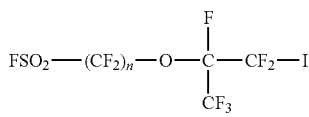

wherein n ranges from 2 to 8. In one embodiment, n is 2. In another embodiment, n is 4.

Also described are fluoropolymers comprising polymerized units of such monomer. The fluoropolymers typically comprise polymerized units of at least one other (e.g. fluorinated) ethylenically unsaturated comonomer, such as tetrafluoroethylene (i.e. TFE). One embodied fluoropolymer may be represented by the formula

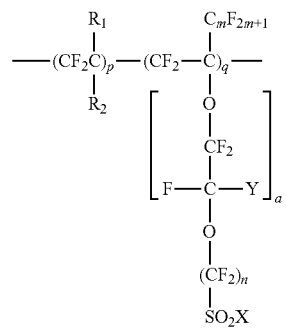

wherein
n ranges from 2 to 8;
Y is F or $C_mF_{2m+1}$;
a is 0, or averages 1 to 2;
m is independently 1, 2, 3, or 4;
X is F or OH;
$R_1$ is H or F;
$R_2$ is H, F or $CF_3$; and
p:q has a ratio ranging from 9:1 to 1:1.

Also described is a fuel cell membrane comprising a support and an embodied fluoropolymer, membrane electrode assemblies, and methods of making fluoropolymers.

DETAILED DESCRIPTION

Description of Monomer & Synthesis

Presently described is a monomer of the formula:

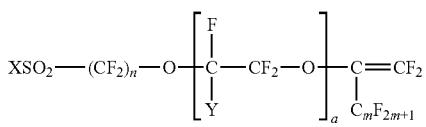

wherein
n ranges from 2 to 8;
Y is F or $C_mF_{2m+1}$;
a is 0, or averages 1 to 2;
m is independently 1, 2, 3, or 4; and
X is F or OH.

In one embodiment, m is 1. In one embodiment, a is 0. In one embodiment, n is 2, 3, or 4. In other embodiments, n is 5, 6, 7, or 8. The number of $CF_2$ repeat units, n, can also be any interval within the range of 2 to 8, such as 2-4 or 3-4.

In some embodiments, the energy barrier to abstract a fluorine atom by a hydrogen atom (H·) from the $C_mF_{2m+1}$ of the ethylenically unsaturated group is greater than the energy barrier to abstract a fluorine atom from $C_mF_{2m+1}$, wherein m is 0. The energy barrier required to break the molecular bonds of the described monomer can be calculated using computational methods such as Density Functional Theory (DFT). Such methods are described in the literature (Yu et al., *J. Am. Chem. Soc.* 2011, 133, 19857-19863). Typically, an (e.g. open-source) software package such as NWChem, such as available from Pacific Northwest National Labs (PNNL), that employs a commonly accepted basis set such as B3LYP/6-311++G(2d,p) is utilized. Reaction barriers are calculated from the difference between the total calculated energy of the molecule of interest and the transition state of that molecule during the fluorine abstraction reaction. In some embodiments, the energy barrier to abstract a fluorine atom by a hydrogen atom (H·) from the $C_mF_{2m+1}$ of the ethylenically unsaturated group is greater 23 kcal/mol. Higher bond strength can provide improved chemical durability.

The monomer can be prepared from any suitable method. For example, the synthesis of perfluoroisopropenyl ether terminated compounds and polymers thereof is described in papers by J. T. Hill (Hill, J. T., *Journal of Fluorine Chemistry*, Volume 9, Issue 2, February 1977, Pages 97-112), Trevor J. Burgess (Burgess, et al., *Chem. Commun.*, 2018, 54, 10439), and I. L Knunyants et al. (Institute of Heteroorganic Compounds, *Academy of Sciences of the USSR* No. 5, pp. 1133-1137, May, 1972.

In some embodiments, the monomer can be prepared by
a) providing a starting monomer having Formula I as
follows:

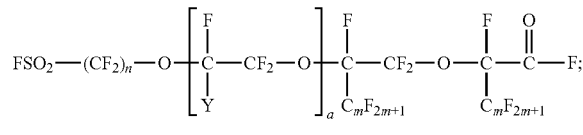

b) reacting the carbonyl fluoride end group of Formula I
with a metal halide (M1$^+$Q$^-$) to form an intermediate
having Formula II as follows (and M1$^+$F$^-$ and carbon
monoxide as a by-product):

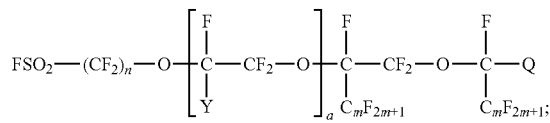

c) heating the intermediate of Formula II to form an
intermediate having Formula III as follows (and per-
fluorocarbonyl halide as a by-product and):

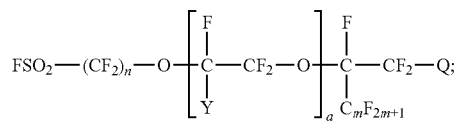

d) reacting the end group of Formula III with an organo-
metallic compound (R-M2) to form a monomer having
Formula IV as follows (and R-Q and M2$^+$F$^-$ as by-
products):

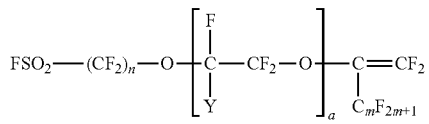

wherein for Formulas I, II, III, and IV
n ranges from 2 to 8;
Y is F or C$_m$F$_{2m+1}$;
a is 0, or averages 1 to 2;
m is independently 1, 2, 3, or 4;
and
Q is Cl, Br, or I.

With regard to step a), a starting monomer having For-
mula I can be made using techniques such as described in
Guerra, U.S. Pat. No. 6,624,328 as depicted in the following
reaction schemes:

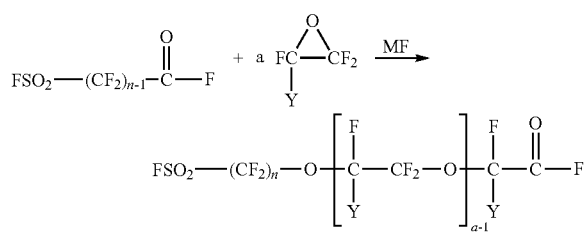

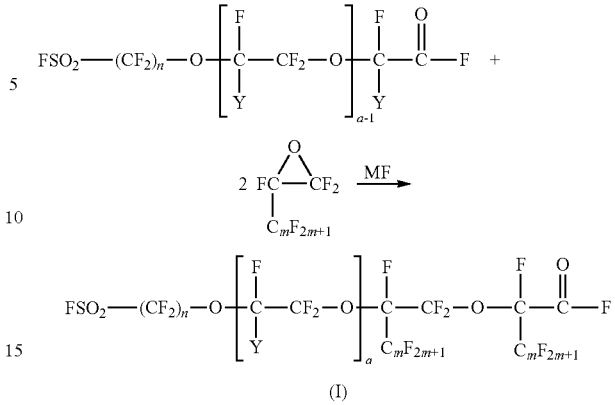

In these reaction schemes, Y can be a fluorine atom or a
C$_m$F$_{2m+1}$ group. For each C$_m$F$_{2m+1}$ group m is independently
1, 2, 3, or 4.

The starting monomer is prepared by (e.g. electrochemi-
cal) fluorination of a sultone as described in U.S. Pat. Nos.
2,732,398 and 4,425,199. Sultone is a 4-7 member ring
according to the formula

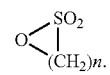

Such reaction produces FSO$_2$—(CF$_2$)$_{n-1}$—COF, which is
then reacted with a fluorinated epoxide compound in the
presence of a catalytic amount of metal fluoride (e.g. CsF,
KF, etc). Some examples of commercially available fluori-
nated epoxide compounds are described in the following
table.

| Y | Epoxide Structure | CAS Name | Available From |
|---|---|---|---|
| F | | 2,2,3,3-Tetrafluorooxirane | BOC Sciences, Shirley, NY, USA |
| CF$_3$ | | Hexafluoropropene oxide (HFPO) | SynQuest Laboratories, Inc. Alachua, FL, USA |
| C$_2$F$_5$ | FC—CF$_2$ \ O / \| C$_2$F$_5$ | 2,2,3-Trifluoro-3-(1,1,2,2,2-pentafluoroethyl) oxirane | Chemieliva Pharmaceutical Co., Ltd. JiangBei Chongqing, China |
| C$_3$F$_7$ | | 2,2,3-Trifluoro-3-(1,1,2,2,3,3,3-heptafluoropropyl) oxirane | SynQuest Laboratories, Inc. Alachua, FL, USA |
| C$_4$F$_9$ | | 2,2,3-Trifluoro-3-(1,1,2,2,3,3,4,4,4-nonafluorobutyl) oxirane | SynQuest Laboratories, Inc. Alachua, FL, USA |

Step b) comprises reacting the carbonyl fluoride end
group of Formula I with a metal halide, M1$^+$Q$^-$, to form a
(e.g. secondary halide) intermediate having Formula II as
depicted in the following reaction scheme:

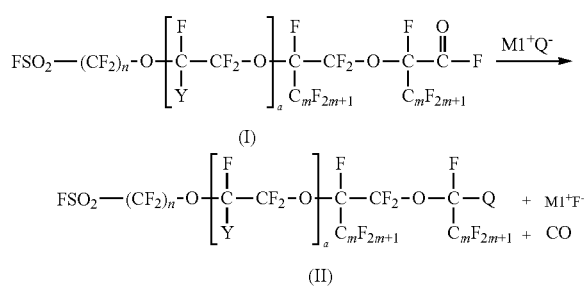

(I)

(II)

In this reaction scheme, n, a, and m are the same as previously described.

As described in *J. Fluor. Chem.*, 2004, 125, 1513-1518, such reaction occurs by heating a mixture of the starting monomer of Formula I having a terminal carbonyl fluoride with a metal halide, such as LiI, LiCl, or LiBr. The reaction mixture may further comprise suitable (dry) polar aprotic solvent, so as to avoid formation of secondary hydrides (e.g. having the terminal group —CF(CF$_3$)—CF$_2$—O—CF(CF$_3$)H). Suitable aprotic solvents include for example acetonitrile, tetrahydrofuran (THF), N,N-dimethylformamide (DMF), N,N-dimethylacetamide (DMAc), dimethylsulfoxide (DMSO), N-methylpyrrolidinone (NMP), methyl tert-butyl ether (MTBE), and combinations thereof. Alternatively, the reaction may be run neat as a slurry. The formation of the secondary iodide begins to take place at approximately 180° C. and liberates carbon monoxide and metal fluoride. The metal fluoride may be removed by filtration and any iodine or molecular halogen formed can be removed by vacuum distillation or copper metal. If the vapor pressure of the starting reagent at 180° C. is low enough to remain a liquid, the procedure may be carried out in glassware under an inert sweep gas such as argon or dry nitrogen. In the case of (CF$_2$)$_n$ with at least n=2 or less, this step preferably in conducted within a stirred pressure reactor to avoid loss of starting material and/or products as vapors.

Step c) comprises heating the (e.g. secondary) intermediate of Formula II to form a (e.g. primary halide) intermediate having Formula III as depicted in the following reaction scheme:

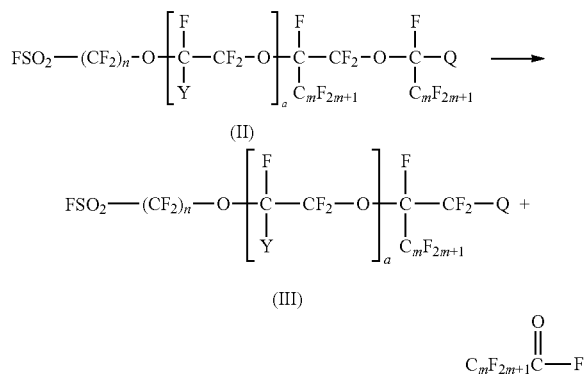

In this reaction scheme, n, a, and m are the same as previously described.

As described in *J. Fluor. Chem.*, 2004, 125, 1513-1518, the method further comprises heating the secondary halide of general structure (II) to a sufficient temperature (e.g. 220° C.) such that the secondary halide of general structure (II) eliminates C$_m$F$_{2m+1}$C(=O)F via beta-elimination to yield the primary halide of the general structure (III). Typically, any remaining solvent is removed prior to heating. The solvent may be removed by application of vacuum and/or reduced pressure. Alternatively, this process may be performed in a solvent that is unreactive to radical intermediates. If the vapor pressure of the starting reagent at 220° C. is low enough to remain a liquid, the procedure may be carried out in glassware under an inert sweep gas such as argon or dry nitrogen. In the case of (CF$_2$)$_n$ with at least n=4 or less, this step is preferably conducted within a stirred pressure reactor to avoid loss of starting material and/or products as vapors. The product is collected, isolated and purified by any suitable means.

Step d) comprises reacting the end group of Formula III with an organometallic compound (R-M2) to form a monomer having Formula IV as follows (and R-Q and M2$^+$F$^-$ as by-products) as depicted in the following reaction scheme:

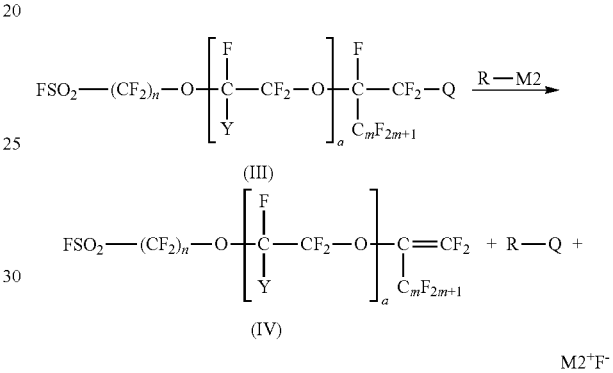

(III)

(IV)

In this reaction scheme, n, a, and m are the same as previously described.

The formation of the isoalkenyl (e.g., isopropenyl) group is accomplished through the nominal elimination of Q and F by production of R-Q and M2$^+$F$^-$, wherein Q can be Br or I. Schematically, this reaction occurs step-wise through reaction with a metalation agent such as zinc, magnesium, or an organometallic compound R-Q (e.g. —CF(CF$_3$)—CF$_2$—Li). In one embodiment, the intermediate of Formula III (e.g. —CF(CF$_3$)—CF$_2$-Q precursor) is transmetallated with the R-M reagent (e.g. PhLi) prior to the final elimination of M2$^+$F$^-$ (e.g. Li—F). The metallized (e.g. lithiated) intermediate is temperature sensitive and thus, this reaction is conducted at low temperatures. In typical embodiments, the reaction temperature is below −45° C. and in some embodiments the reaction temperature is below −55, −65, or −75° C. Preferred organolithium reagents lack hydrogen atoms beta to the lithium position. Thus, phenyl lithium and methyl lithium are preferred organolithium reagents whereas tert-butyl lithium, sec-butyl lithium, and n-butyl lithium are not.

The pyrophoric character of organolithium reagents and the moisture-sensitive nature of the (e.g. —CF(CF$_3$)—CF$_2$—Li) intermediate results in an elimination reaction that is conducted under rigorously dry and air-free conditions (no H$_2$O or O$_2$). Thus, the elimination reaction is conducted under a nitrogen or argon atmosphere.

The elimination reaction is typically conducted in a solvent or mixture of solvents. The solvent(s) used for the reaction must be free of acidic protons and chemical groups that may react with the strongly basic and nucleophilic organo-lithium reagent. For example, solvents containing functional groups such as alcohols, amines, amides, carboxylic acids, ketones, aldehydes, and thiols are typically avoided. Additionally, the low temperature required for the lithiation reaction imposes limitations concerning solvent selection. The solvent or solvent mixture used for the elimination reaction must possess a freezing point below the reaction temperature (e.g. −78° C.) and be capable of solubilizing the lithium reagent as well as the precursor (e.g. —CF(CF$_3$)—CF$_2$-Q) material. A biphasic solvent system comprising an organic solvent to solubilize the organolithium reagent and a fluorinated solvent to solubilize the precursor (e.g.—CF(CF$_3$)—CF$_2$-Q) may be used. Preferred solvents are hexanes, perfluorohexanes, and diethyl ether.

In some embodiments, the method further comprises reacting the F group of the terminal FSO$_2$ group of Formula IV with a base, such as a metal (e.g. potassium) hydroxide followed by ion exchange with a strong acid, such as HCl or an ion exchange resin such as Amberlyst 15 (Rohm and Hass), to form a monomer having Formula V as follows:

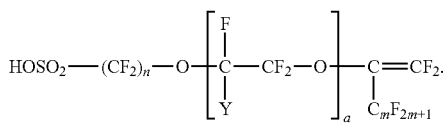

The above reaction schemes produce various (e.g. intermediate) compounds of Formulas I, II, III, IV and V. Some notable (e.g. iodide) compounds of Formula IV include for example

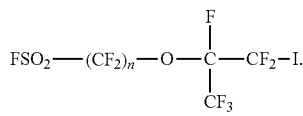

Specific compounds include

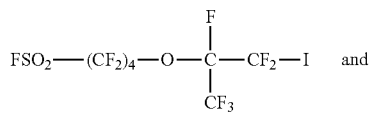

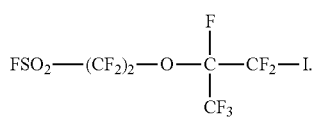

Methods of Making Fluoropolymers

Fluoropolymers can be prepared from the sulfonyl fluoride monomers described herein. The fluoropolymer comprises polymerized units of at least one monomer, as described herein. The fluoropolymer typically further comprises polymerized units of at least one other (i.e. different) ethylenically unsaturated comonomer. In some embodiments, the fluoropolymer comprises polymerized units of at least one fluorinated or perfluorinated ethylenically unsaturated comonomer.

Common fluorinated comonomers utilized for making fluoropolymer include for example (per)fluorinated alkenes such as tetrafluoroethylene (TFE), vinylidene fluoride (VF), hexafluoropropylene (HFPO), and other (per)fluorinated vinyl ether monomers.

The fluoropolymer typically comprises 5 to 50 mol % of one or more polymerized fluorinated sulfonyl monomers, at least a portion or the totality of polymerized fluorinated sulfonyl monomers comprising a fluorinated sulfonyl monomer as described herein. The mol % is based on the total moles of polymerized monomers of the fluoropolymer. In some embodiments, the fluoropolymer comprises at least 6, 7, 8, 9, 10, 11, 12, 13, 14, 15, 16, 17, 18, 19, or 20 mol % polymerized fluorinated sulfonyl monomers, as described herein. In some embodiments, the fluoropolymer comprises less than 45, 40, 35, 30, or 25 mol % of one or more polymerized sulfonyl monomers as described herein.

In one embodiment, the fluoropolymer is a copolymer of a fluorinated sulfonyl monomer as described herein and TFE.

The fluoropolymer typically has at least 50 mol % of the polymerized (e.g. repeat) units of —[CF$_2$—CF$_2$]—, derived from the polymerization of tetrafluoroethylene (TFE). In some embodiments, the fluoropolymer comprises at least 50, 55, 60, 65, 70, 75, 80, 90 or 95 mol % of polymerized units of —[CF$_2$—CF$_2$]—, based on the total moles of polymerized monomers of the fluoropolymer.

When the fluoropolymer is a copolymer of TFE and one or more fluorinated sulfonyl monomers as described herein, the fluoropolymer can be represented by Formula VII as follows:

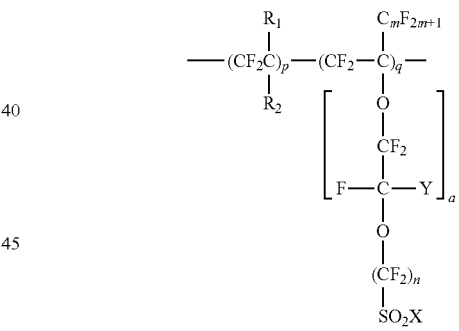

wherein n ranges from 2 to 8;

Y is F or C$_m$F$_{2m+1}$;

a is 0, or averages 1 to 2;

m is independently 1, 2, 3, or 4;

X is F or OH;

R$_1$ is H or F;

R$_2$ is H or F or CF$_3$; and p:q has a ratio ranging from 1:1 to 9:1.

In some embodiments, the ratio of p:q is at least 2:1, 2.5:1, 3:1, 3.5:1, 4:1, 4.5:1, 5:1, 5, 5:1, 6:1, 6.5:1, 7:1, 7.5:1, 8:1. The values of p and q are typically an average value for the fluoropolymer. Thus, p and q are typically not integers.

Some illustrative fluoropolymers are depicted as follows

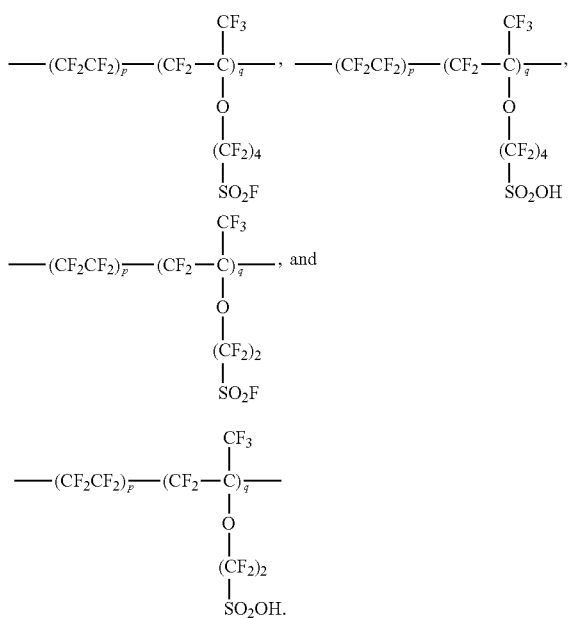

The fluoropolymer can be made by any suitable method. Some embodied methods of preparing fluoropolymers and various comonomers are described in U.S. Pat. No. 7,348,088 and WO 2017/053563; incorporated herein by reference.

The fluoropolymer is typically prepared by (e.g. free-radical) solution or emulsion polymerization. One embodiment method of making a fluoropolymer comprises emulsifying at least one fluorinated sulfonyl monomer, as described herein, in an aqueous liquid; optionally emulsifying at least one ethylenically unsaturated comonomer in the aqueous liquid; charging a polymerization kettle with the aqueous liquid of emulsified monomer(s); and heating the aqueous liquid of emulsified monomer under pressure in the presence of an initiator such that the monomers polymerize forming a fluoropolymer. Useful polymerization temperatures can range from 20° C. to 150° C. Typically, polymerization is carried out in a temperature range from 40° C. to 120° C., 40° C. to 100° C., or 50° C. to 80° C. The polymerization pressure is usually in the range of 0.8 MPa to 2.5 MPa, 1.0 MPa to 2.5 MPa, and in some embodiments is in the range from 1.0 MPa to 2.0 MPa.

In some embodiments, the method further comprises separating the (e.g. coagulated) fluoropolymer from the aqueous liquid. In some embodiments, (per)fluorinated emulsifiers may be useful. Generally, these fluorinated emulsifiers are present in a range from about 0.02% to about 3% by weight with respect to the polymer. Polymer particles produced with a fluorinated emulsifier typically have an average diameter, as determined by dynamic light scattering techniques, in range of about 10 nanometers (nm) to about 300 nm, and in some embodiments in range of about 50 nm to about 200 nm. The obtained fluoropolymer dispersion can be subject to optional ion exchange purification and concentrated if desired.

In some embodiments, the method further comprises one or more steps comprising hydrolyzing, ion exchanging with an acid, drying and dispersing the fluoropolymer in a mixture of alcohol and water.

In some embodiments, the method comprises hydrolyzing and dispersing the polymer in one step at elevated temperature and pressure with LiOH, NaOH, KOH, etc. followed by ion exchanging with an acid to make the proton form. This aqueous dispersion can then be solvent exchanged with alcohols such as methanol, ethanol, IPA, nPA, etc, to make a coating dispersion. Alternatively, the ion exchanged aqueous dispersion can be dried to solid under mild conditions and the step of dispersing the (e.g. dried solid) fluoropolymer in an alcohol/water mixture to make a coating solution.

Typically, the ionic fluoropolymer dispersion to be used to form a membrane has an ionic fluoropolymer concentration of at least 20, 30, or 40 percent by weight. Further details concerning aqueous emulsion polymerization of fluoropolymers are described in previously cited WO 2017/053563.

The fluoropolymer typically has an equivalent weight (EW) of at least 600, 700, 750, or 800 g/equivalent of sulfonic acid. In some embodiments, the fluoropolymer has an equivalent weight (EW) of greater than 800, more typically greater than 900, more typically greater than 1000. In some embodiments, the fluoropolymer typically has an equivalent weight (EW) of less than 1200, more typically less than 1100. The equivalent weight can be determined by combining approximately 0.5-0.7 g of the dried fluoropolymer (e.g. membrane) in the proton form with 50 g 1 M NaCl(aq). The dried fluoropolymer can be ion exchanged for more than 4 hours with gentle agitation by rolling or shaking in a bottle. The HCl generated can be titrated with 0.03 M NaOH to determine the ion exchange capacity of films with known mass.

The physical properties of the fluoropolymer can be evaluated with various test method known in the art. A commonly accepted accelerated durability test is the Open Circuit Voltage (OCV) test as described by the United States Department of Energy (US DOE Hydrogen and Fuel Cell Technologies Office; Multi-Year Research, Development, and Demonstration Plan (2017), Section 3.4 Fuel Cells). In such method, a 25-50 cm$^2$ fuel cell is operated at open circuit voltage (OCV) at 90° C. with both anode and cathode relative humidity set at 30%. Fuel ($H_2$) and oxidant (air) stoichiometries are set to 10 based on 0.2 A/cm$^2$ equivalent flow. Outlet pressures for both anode and cathode are set to 150 kPa absolute. End of life is determined when the cell OCV potential decays by 20% or more of the original OCV.

The fluoropolymers described herein are surmised to have good ion transport and electrical resistance properties, and to function as gas crossover barriers. Each of these properties can be measured using known methods. For example, Cooper, *J Electrochem. Soc.*, 157 (11) B1731-B1739 (2010) describes a test method used to measure membrane ion transport resistance and related ion conductivity. The test procedure for the through-plane resistance measurement consists of measuring the sample thickness, assembling it into a test fixture with two or four electrodes (typically platinum wires spaced 1 cm apart), conditioning the membrane at the desired test temperature and RH, and obtaining an alternating current (AC) impedance spectrum of the sample. The temperature and humidity can be changed, and the measurement repeated to characterize the sample at a variety of temperature and humidity combinations. Ionic conductivity is calculated from the measured resistance (R) (i.e. AC impedance), length between electrodes (L), and cross-sectional area (A):

$$\text{Conductivity} = L/(R*A)$$

Hydrogen crossover and electrical short resistance can be measured using cyclic voltammetry as described in Schoemaker et al., FUEL CELLS 14, 2014, No. 3, 412-415. The cathode is supplied with humidified nitrogen and the anode is supplied with humidified hydrogen, A potentiostat is used to apply voltages between about 0.085 V and about 0.650 V at a scan rate of about 0.1 to 2 mVs$^{-1}$ and the resultant current density is measured in A/cm$^2$. The potential range between 0.4 and 0.6 V is fitted with a linear plot wherein the slope of the line represents the electrical resistance (i.e. short resistance) of the membrane and the intercept represents the hydrogen cross-over current density in A/cm$^2$.

Articles

The fluorinated sulfonyl monomers and fluoropolymers described herein can be used in place of known fluorinated sulfonyl monomers and fluoropolymers that typically comprise a tertiary F in place of the $C_mF_{2m+1}$ group.

One illustrative use for such fluoropolymers (e.g. TFE copolymer) is ion conducting membranes or catalyst ink for use in fuel cells or other electrolytic cells. A membrane electrode assembly (MEA) is the central element of a proton exchange membrane fuel cell, such as a hydrogen fuel cell. Fuel cells are electrochemical cells that produce usable electricity by the catalyzed combination of a fuel such as hydrogen and an oxidant such as oxygen. Typical MEA's comprise a polymer electrolyte membrane (also known as an ion conductive membrane (ICM)), which functions as a solid electrolyte. One particular type of ICM is a proton exchange membrane, (PEM). One face of the ICM or PEM is in contact with an anode electrode layer and the opposite face is in contact with a cathode electrode layer. Each electrode layer includes electrochemical catalysts, typically including platinum metal or alloys of platinum metal. Gas diffusion layers (GDL's) facilitate gas transport to and from the anode and cathode electrode materials and conduct electrical current. The GDL may also be called a fluid transport layer (FTL) or a diffuser/current collector (DCC). The anode and cathode electrode layers may be applied to GDL's in the form of a catalyst ink, and the resulting coated GDL's sandwiched with a PEM to form a five-layer MEA. Alternately, the anode and cathode electrode layers may be applied to opposite sides of the PEM in the form of a catalyst ink, and the resulting catalyst-coated membrane (CCM) sandwiched with two GDL's to form a five-layer MEA. Details concerning the preparation of catalyst inks and their use in membrane assemblies can be found, for example, in U.S. Pat. Publ. No. 2004/0107869 (Velamakanni et al.). In a typical PEM fuel cell, protons are formed at the anode via hydrogen oxidation and transported across the PEM to the cathode to react with oxygen, causing electrical current to flow in an external circuit connecting the electrodes. The PEM forms a durable, non-porous, electrically non-conductive mechanical barrier between the reactant gases, yet it also passes H$^+$ ions readily.

The fluoropolymers described herein are useful as a PEM and/or useful for making a membrane or catalyst ink composition.

In some embodiments, the copolymer of the present disclosure may be useful for making a polymer electrolyte membrane. The copolymer may be formed into a polymer electrolyte membrane by any suitable method, including casting, molding, and extrusion. See for example previously cited U.S. Pat. No. 7,348,088. Typically, the membrane is cast from a fluoropolymer dispersion (e.g., those described above in any of their embodiments) and then dried, annealed, or both. The copolymer may be cast from a suspension. Any suitable casting method may be used, including bar coating, spray coating, slit coating, and brush coating. After forming, the membrane may be annealed, typically at a temperature of 120° C. or higher, more typically 130° C. or higher, most typically 150° C. or higher. In some embodiments of the method according to the present disclosure, a polymer electrolyte membrane can be obtained by obtaining the copolymer in a fluoropolymer dispersion, optionally purifying the dispersion by ion-exchange purification, and concentrating the dispersion to make a membrane. Typically, if the fluoropolymer dispersion is to be used to form a membrane, the concentration of copolymer is advantageously high (e.g., at least 20, 30, or 40 percent by weight). Often a water-miscible organic solvent is added to facilitate film formation. Examples of water-miscible solvents include lower alcohols (e.g., methanol, ethanol, isopropanol, n-propanol), polyols (e.g., ethylene glycol, propylene glycol, glycerol), ethers (e.g., tetrahydrofuran and dioxane), ether acetates, acetonitrile, acetone, dimethylsulfoxide (DMSO), N,N dimethylacetamide (DMA), ethylene carbonate, propylene carbonate, dimethylcarbonate, diethylcarbonate, N,N-dimethylformamide (DMF), N-methylpyrrolidinone (NMP), dimethylimidazolidinone, butyrolactone, hexamethylphosphoric triamide (HMPT), isobutyl methyl ketone, sulfolane, and combinations thereof.

In another embodiment, a fluoropolymer (e.g. TFE copolymer) dispersion as described herein can be combined with catalyst particles (e.g., metal particles or carbon-supported metal particles) to form a catalyst ink. A variety of catalysts may be useful. Typically, carbon-supported catalyst particles are used. Typical carbon-supported catalyst particles are 30% to 95% carbon and 5% to 70% catalyst metal by weight, the catalyst metal typically comprising platinum for the cathode and platinum or platinum and ruthenium in a weight ratio of 2:1 for the anode. However, other metals may be useful, for example, gold, silver, palladium, iridium, rhodium, iron, cobalt, nickel, chromium, tungsten, manganese, vanadium, and alloys thereof. To make an MEA or CCM, catalyst may be applied to the PEM by any suitable means, including both hand and machine methods, including hand brushing, notch bar coating, fluid bearing die coating, wire-wound rod coating, slot-fed knife coating, three-roll coating, or decal transfer. Coating may be achieved in one application or in multiple applications. Advantageously, copolymers according to the present disclosure may be useful for making a catalyst layer with one coating application. The catalyst ink may be applied to a PEM or a GDL directly, or the catalyst ink may be applied to a transfer substrate, dried, and thereafter applied to the PEM or to the FTL as a decal.

In some embodiments, the catalyst ink includes the copolymer disclosed herein at a concentration of at least 10, 15, or 20 percent by weight and up to 30 percent by weight, based on the total weight of the catalyst ink. In some embodiment, the catalyst ink includes the catalyst particles in an amount of at least 10, 15, or 20 percent by weight and up to 50, 40, or 30 percent by weight, based on the total weight of the catalyst ink. The catalyst particles may be added to the fluoropolymer dispersion made as described above in any of its embodiments. The resulting catalyst ink may be mixed, for example, with heating. The percent solids in the catalyst ink may be selected, for example, to obtain desirable rheological properties. Examples of suitable organic solvents useful for including in the catalyst ink include lower alcohols (e.g., methanol, ethanol, isopropanol, n-propanol), polyols (e.g., ethylene glycol, propylene glycol, glycerol), ethers (e.g., tetrahydrofuran and dioxane), diglyme, polyglycol ethers, ether acetates, acetonitrile, acetone, dimethylsulfoxide (DMSO), N,N dimethylacetamide (DMA), ethylene carbonate, propylene carbonate, dimethylcarbonate, diethylcarbonate, N,N-dimethylformamide (DMF), N-methylpyrrolidinone (NMP), dimethylimidazolidinone, butyrolactone, hexamethylphosphoric triamide (HMPT), isobutyl methyl ketone, sulfolane, and combinations thereof. In some embodiments, the catalyst ink contains 0% to 50% by weight of a lower alcohol and 0% to 20% by weight of a polyol. In addition, the ink may contain 0% to 2% of a suitable dispersant.

In some embodiments of the polymer electrolyte membrane of the present disclosure, a salt of at least one of cerium, manganese or ruthenium, or one or more cerium oxide or zirconium oxide compounds is added to the acid form of the copolymer before membrane formation. Typically, the salt of cerium, manganese, or ruthenium and/or the cerium or zirconium oxide compound is mixed well with or dissolved within the copolymer to achieve substantially uniform distribution.

The salt of cerium, manganese, or ruthenium may comprise any suitable anion, including chloride, bromide, hydroxide, nitrate, sulfonate, acetate, phosphate, and carbonate. More than one anion may be present. Other salts may be present, including salts that include other metal cations or ammonium cations. Once cation exchange occurs between the transition metal salt and the acid form of the ionomer, it may be desirable for the acid formed by combination of the liberated proton and the original salt anion to be removed. Thus, it may be useful to use anions that generate volatile or soluble acids, for example chloride or nitrate. Manganese cations may be in any suitable oxidation state, including $Mn^{2+}$, $Mn^{3+}$, and $Mn^{4+}$, but are most typically $Mn^{2+}$. Ruthenium cations may be in any suitable oxidation state, including $Ru^{3+}$ and $Ru^{4+}$, but are most typically $Ru^{3+}$. Cerium cations may be in any suitable oxidation state, including $Ce^{3+}$ and $Ce^{4+}$. Without wishing to be bound by theory, it is believed that the cerium, manganese, or ruthenium cations persist in the polymer electrolyte because they are exchanged with $H^+$ ions from the anion groups of the polymer electrolyte and become associated with those anion groups. Furthermore, it is believed that polyvalent cerium, manganese, or ruthenium cations may form ionic crosslinks between anion groups of the polymer electrolyte, further adding to the stability of the polymer. In some embodiments, the salt may be present in solid form. The cations may be present in a combination of two or more forms including solvated cation, cation associated with bound anion groups of the polymer electrolyte membrane, and cation bound in a salt precipitate. The amount of salt added is typically between 0.001 and 0.5 charge equivalents based on the molar amount of acid functional groups present in the polymer electrolyte, more typically between 0.005 and 0.2, more typically between 0.01 and 0.1, and more typically between 0.02 and 0.05. Further details for combining an anionic copolymer with cerium, manganese, or ruthenium cations can be found in U.S. Pat. Nos. 7,575,534 and 8,628,871, each to Frey et al. and U.S. Pat. No. 9,023,496, "Durable Fuel Cell. Fuel cell Membrane Electrode Assembly with Combined Additives", Pierpont et al.

Useful cerium oxide compounds may contain cerium in the (IV) oxidation state, the (III) oxidation state, or both and may be crystalline or amorphous. The cerium oxide may be, for example, $CeO_2$ or $Ce_2O_3$. The cerium oxide may be substantially free of metallic cerium or may contain metallic cerium. The cerium oxide compound may or may not contain other metal elements. Examples of mixed metal oxide compounds comprising cerium oxide include solid solutions such as zirconia-ceria and multicomponent oxide compounds such as barium cerate. Without wishing to be bound by theory, it is believed that the cerium oxide may strengthen the polymer by chelating and forming crosslinks between bound anionic groups. The amount of cerium oxide compound added is typically between 0.01 and 5 weight percent based on the total weight of the copolymer, more typically between 0.1 and 2 weight percent, and more typically between 0.2 and 0.3 weight percent. The cerium oxide compound is typically present in an amount of less than 1% by volume relative to the total volume of the polymer electrolyte membrane, more typically less than 0.8% by volume, and more typically less than 0.5% by volume. Cerium oxide may be in particles of any suitable size, in some embodiments, between 1 nm and 5000 nm, 200 nm to 5000 nm, or 500 nm to 1000 nm. Further details regarding polymer electrolyte membranes including cerium oxide compounds can be found in U.S. Pat. No. 8,367,267 (Frey et al.).

The polymer electrolyte membrane, in some embodiments, may have a thickness of up to 90 micrometers, up to 60 micrometers, or up to 30 micrometers. A thinner membrane may provide less resistance to the passage of ions. In fuel cell use, this results in cooler operation and greater output of usable energy.

In some embodiments, a fluoropolymer (e.g. TFE copolymer) as described herein may be imbibed into a porous supporting matrix, typically in the form of a thin membrane having a thickness of up to 90 micrometers, up to 60 micrometers, or up to 30 micrometers. Any suitable method of imbibing the copolymer into the pores of the supporting matrix may be used, including overpressure, vacuum, wicking, and immersion. Any suitable supporting matrix may be used. Typically, the supporting matrix is electrically non-conductive. Typically, the supporting matrix is composed of a fluoropolymer, which is more typically perfluorinated. Typical matrices include porous polytetrafluoroethylene (PTFE), such as biaxially stretched PTFE webs. In another embodiment fillers (e.g., fibers) might be added to the polymer to reinforce the membrane.

The membranes can be fabricated to include a mechanical reinforcement support such as expanded poly(tetrafluoroethylene) (ePTFE) as described in U.S. Pat. No. 5,599,614 "Integral Composite Membrane", Bahar et al. Alternatively, an electrospun nanofiber may be used, as described in US 2013/0101918 A1 "Reinforced Polymer Electrolyte Membrane", Yandrasits et al. Membrane thickness including such support can range from 5 to 500 micrometers in thickness.

To make an MEA, GDL's may be applied to either side of a CCM by any suitable means. Any suitable GDL may be used in the practice of the present disclosure. Typically, the GDL support is comprised of sheet material comprising carbon fibers. Typically, the GDL is a carbon fiber construction selected from woven and non-woven carbon fiber constructions. Carbon fiber constructions that may be useful include Toray™ Carbon Paper, SpectraCarb™ Carbon Paper, AFN™ non-woven carbon cloth, and Zoltek™ Carbon Cloth. The GDL may be coated or impregnated with various materials, including carbon particle coatings, hydrophilizing treatments, and hydrophobizing treatments such as coating with polytetrafluoroethylene (PTFE).

In use, the MEA is typically sandwiched between two rigid plates, known as distribution plates, also known as bipolar plates (BPP's) or monopolar plates. Like the GDL, the distribution plate is typically electrically conductive. The distribution plate is typically made of a carbon composite, metal, or plated metal material. The distribution plate distributes reactant or product fluids to and from the MEA electrode surfaces, typically through one or more fluid-conducting channels engraved, milled, molded or stamped in the surface(s) facing the MEA(s). These channels are sometimes designated a flow field. The distribution plate may distribute fluids to and from two consecutive MEA's in a stack, with one face directing fuel to the anode of the first MEA while the other face directs oxidant to the cathode of the next MEA (and removes product water), hence the term "bipolar plate." Alternately, the distribution plate may have channels on one side only, to distribute fluids to or from an MEA on only that side, which plate may be termed a "monopolar plate." A typical fuel cell stack comprises a number of MEA's stacked alternately with bipolar plates.

Another type of electrochemical device is an electrolysis cell, which uses electricity to produce chemical changes or chemical energy. An example of an electrolysis cell is a chlor-alkali membrane cell where aqueous sodium chloride is electrolyzed by an electric current between an anode and a cathode. The electrolyte is separated into an anolyte portion and a catholyte portion by a membrane subject to harsh conditions. In chlor-alkali membrane cells, caustic sodium hydroxide collects in the catholyte portion, hydrogen gas is evolved at the cathode portion, and chlorine gas is evolved from the sodium chloride-rich anolyte portion at the anode. The copolymer of the present disclosure may be useful, for example, in the manufacture of catalyst ink and electrolyte membranes for use in chlor-alkali membrane cells or other electrolytic cells. Another type of electrolysis cell uses electricity to produce hydrogen and oxygen where water is electrolyzed by an electric current between an anode and a cathode.

The copolymer according to the present disclosure may also be useful as a binder for an electrode in other electrochemical cells (for example, lithium ion batteries). To make electrodes, powdered active ingredients can be dispersed in a solvent with the copolymer and coated onto a metal foil substrate, or current collector. The resulting composite electrode contains the powdered active ingredient in the polymer binder adhered to the metal substrate. Useful active materials for making negative electrodes include alloys of main group elements and conductive powders such as graphite. Examples of useful active materials for making a negative electrode include oxides (tin oxide), carbon compounds (e.g., artificial graphite, natural graphite, soil black lead, expanded graphite, and scaly graphite), silicon carbide compounds, silicon-oxide compounds, titanium sulfides, and boron carbide compounds. Useful active materials for making positive electrodes include lithium compounds, such as $Li_{4/3}Ti_{5/3}O_4$, $LiV_3O_8$, $LiV_2O_5$, $LiCo_{0.2}N_{0.8}O_2$, $LiNiO_2$, $LiFePO_4$, $LiMnPO_4$, $LiCoPO_4$, $LiMn_2O_4$, and $LiCoO_2$. The electrodes can also include electrically conductive diluents and adhesion promoters.

Electrochemical battery cells (for example, lithium ion batteries) including the copolymer disclosed herein as a binder or solid polymer electrolyte can be made by placing at least one each of a positive electrode and a negative electrode in contact with an electrolyte. Typically, a microporous separator imbibed with liquid electrolyte can be used to prevent the contact of the negative electrode directly with the positive electrode. The copolymer disclosed herein may be suitable to serve as the electrolyte and separator. Once the electrodes are connected externally, lithiation and delithiation can take place at the electrodes, generating a current.

The electrochemical cells can be useful as rechargeable batteries and can be used in a variety of devices, including portable computers, tablet displays, personal digital assistants, mobile telephones, motorized devices (e.g., personal or household appliances and vehicles), instruments, illumination devices (e.g., flashlights) and heating devices. One or more of the electrochemical cells can be combined to provide a battery pack.

EXAMPLES

| Abbreviation or Trade Name | Description | Source |
|---|---|---|
| Potassium Fluoride (KF) | >99% | Sigma Aldrich Co. LLC., St. Louis, MO |
| Tetraglyme | Tetraethylene glycol dimethyl ether | Sigma Aldrich Co. LLC., St. Louis, MO |
| Adiponitrile | 99% 1,4-Dicyanobutane | Sigma Aldrich Co. LLC., St. Louis, MO |
| Hexafluoropropylene oxide 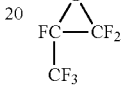 | reagent | Chemours, Wilmington, DE |
| Lithium Iodide (LiI) | reagent | Alfa Aesar, Tewksbury, Massachusetts |
| FLUORINERT 72 | solvent | 3M Company, Maplewood MN |
| Hexane | reagent | Sigma-Aldrich Co. LLC., St. Louis, Missouri |
| PhLi | Phenyl lithium, 1.9M in dibutyl ether | Sigma-Aldrich Co. LLC., St. Louis, Missouri |
| Hexanes | 98+%, mixed isomers | Alfa Aesar, Tewksbury, Massachusetts |
| Perfluorohexanes | 98+% | Alfa Aesar, Tewksbury, Massachusetts |
| Acetic Acid | Glacial, AX0073P-5 | Available from EMD Millipore, Billerica, Massachusetts |
| Basic Alumina | Aluminum oxide, activated, basic | Sigma-Aldrich Co. LLC., St. Louis, Missouri |
| $CaH_2$ | Calcium hydride, reagent grade, 95% | Sigma-Aldrich Co. LLC., St. Louis, Missouri |
| $MgSO_4$ | Anhydrous, MX-0075-1 | EMD Millipore, Billerica, Massachusetts |
| Sodium Bisulfite | Reagent | MCB Manufacturing Chemists, Inc., Cincinnati, Ohio |
| 8-fluorosulfonyl-perfluoro(2,5-dimethyl-3,6-dioxaoctanoyl) fluoride | CAS#4089-58-1, E25151, 95% | Manchester Organics, Runcorn, Cheshire, Wales, UK |
| Deionized Water | | Thermo Scientific Barnstead Genpure system |
| 0.5M HCl | Reagent | Sigma-Aldrich Co. LLC., St. Louis, Missouri |

Preparatory Example 1: Synthesis of Starting Monomer of Formula I, $FSO_2C_4F_8OCF(CF_3)$ $CF_2OCF(CF_3)C(O)F$

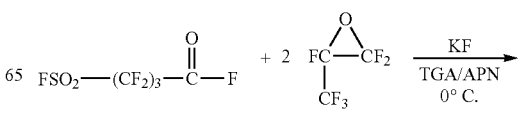

-continued

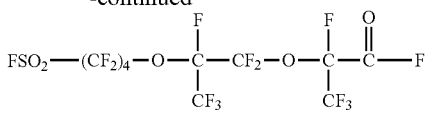

Butane sultone was electrochemically fluorinated in hydrofluoric acid (HF) as described in U.S. Pat. Nos. 2,732,398 and 4,425,199 to give perfluorosulfonyl fluoride butyryl fluoride, $FSO_2C_3F_6COF$. A 600 ml PARR reactor (Parr Instrument Company, Moline, Illinois) was first charged with 10 g, 0.2 mol spray dried KF available from Sigma Aldrich sealed and evacuated to 25 mm vacuum. Vacuum charged 350 g, 1.3 mol perfluorosulfonyl fluoride butyryl fluoride along with 50 g of tetraglyme (i.e. tetraethylene glycol dimethyl ether) and 50 g adiponitrile $((CH_2)_4(CN)_2$ available from Sigma Aldrich). The reactor was stirred and cooled to 0° C. 400 g, 2.4 mol hexafluoropropylene oxide, available from Chemours Company, was metered into the reactor over three hours. The reactor was warmed to 25° C. and the mixture was drained. Distillation by column fractionation gave 292 g, 0.4 mol $FSO_2C_4F_8OCF(CF_3)CF_2OCF(CF_3)COF$ having a 96° C. boiling point at 50 mm Hg.

Example 1: Synthesis of $FSO_2C_4F_8OCF(CF_3)CF_2I$

Synthetic example monomer of precursor perfluoro (2-iodo-isopropoxy)butylsulfonyl fluoride was provided by the following reaction scheme:

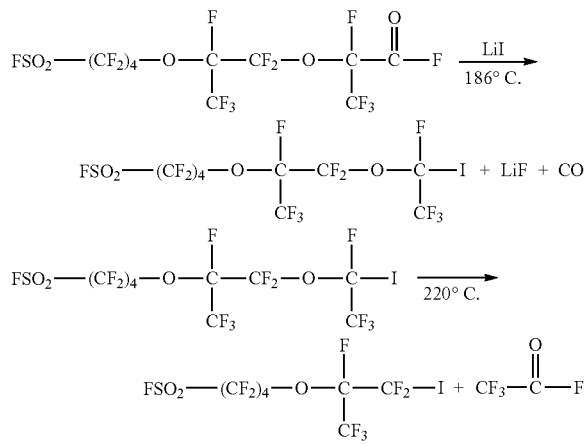

Although the reaction scheme depicts two hexafluoropropylene oxide (HFPO) units, the starting compound has a distribution of HFPO units ranging from 0 to 3.

A 3-neck 500 ml round bottom flask equipped with a mechanical stirrer, condenser and a thermocouple was charged with 100 g, 0.2 mol $FSO_2C_4F_8OCF(CF_3)CF_2OCF(CF_3)COF$ and 22 g, 0.2 mol LiI (Alfa Aesar Chemical) and heated to 186° C. for 2 hours. The reactor was cooled to 25° C. and 84 g, 0.12 mol $FSO_2C_4F_8OCF(CF_3)CF_2OCF(CF_3)I$ was recovered after filtration. Thermolysis in a 600 ml PARR reactor was done with 51 g, 0.1 mol $FSO_2C_4F_8OCF(CF_3)CF_2OCF(CF_3)I$ heated to 220° C. for 2 hours. The reactor was cooled down to 25° C., vented and 42 g, 0.1 mol $FSO_2C_4F_8OCF(CF_3)CF_2I$ was drained. The red colored liquid product was washed with aqueous sodium bisulfate and vacuum distilled to give a boiling point of 98° C. at 52 mm vacuum.

Example 2: Synthesis of $FSO_2C_4F_8OC(CF_3)=CF_2$

Synthetic example monomer of perfluoroisopropenyl ether butane sulfonyl fluoride (designated MV(CH3)4S) was provided by the following reaction scheme:

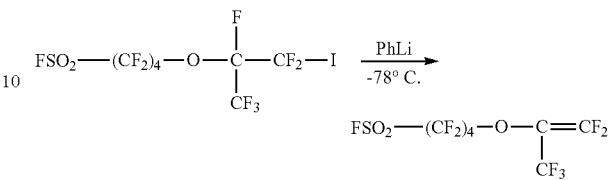

PhLi was used as dried powder obtained by removing dibutyl ether under high vacuum. Hexanes were dried by stirring over sodium metal for 24 hours prior to filtration under inert nitrogen atmosphere. Perfluorohexane was dried by stirring over $CaH_2$ for 12 hours prior to degassing with three freeze-pump-thaw cycles under high vacuum. Perfluorohexane was then collected by vacuum transfer from $CaH_2$. $FSO_2C_4F_8OC_3F_6I$ was first degassed with three freeze-pump-thaw cycles under high vacuum before being filtered under inert nitrogen atmospheres through dried basic alumina.

In a glovebox, PhLi (38 mmol) and hexanes (100 mL) were added to a 250 mL Schlenk flask with a stir bar. The flask was then capped with a rubber septum. In a separate 100 mL Schlenk flask, $FSO_2C_4F_8OC_3F_6I$ (20.16 g, 40 mmol) and perfluorohexanes (30 mL) were combined. Both reagent flasks were then sealed, removed from the glovebox, and connected to a Schlenk line using standard Schlenk techniques. Using a dry ice/IPA cold bath, both flasks were then cooled to −78° C. Once cooled, the perfluorohexane solution was cannula transferred to the flask containing PhLi under rapid stirring. Upon addition of the perfluorohexane solution, a waxy white precipitate formed. Once addition was complete, the reaction was allowed to gradually warm to room temperature under Ar (~6 hours). An opaque, heterogenous, light yellow solution was formed. The reaction was then quenched with 5 mL distilled water before being transferred to a separatory funnel. Additional perfluorohexanes (20 mL) were added and the lower, fluorous phase was washed sequentially with hexanes, 1 M aqueous acetic acid, saturated sodium bicarbonate, and distilled water. The washed fluorous phase was then dried with $MgSO_4$ prior to filtration and solvent removal under reduced pressure (rotovap). Isopropenyl sulfonyl fluoride was obtained at a 31% yield (4.8 g).

Example 3: Synthesis of $FSO_2C_2F_4OCF(CF_3)CF_2I$

Synthetic example monomer of precursor perfluoro (2-iodo-isopropoxy)ethylsulfonyl fluoride was provided by the following reaction scheme:

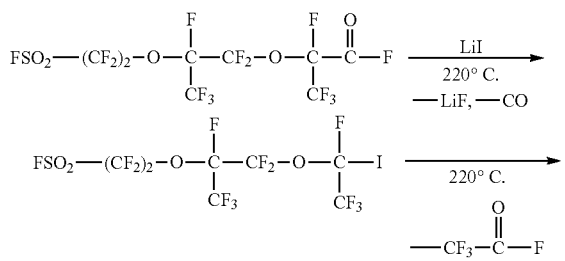

-continued

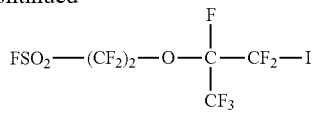

A clean 600 mL stirred pressure reactor (Parr Inst. Co., Moline, IL) was dried with purged $N_2(g)$ while heating to an internal gas temperature of 160° C. and then cooled to room temperature under flowing dry $N_2(g)$. In a nitrogen purged box, the dried reactor was charged with 29.49 g, (220 mmol) lithium iodide (LiI) followed by 72.53 g (122 mmol) of the precursor acid fluoride, $FSO_2C_2F_4OCF(CF_3)CF_2OCF(CF_3)$ COF. The solution immediately turned light yellow in the reactor. The reactor was then sealed and placed into a heating mantle and fitted with overhead stirring. The mixture was heated to a set point of 220° C. with an initial excursion up to 240° C., in which temperature was above 220° C. for 20 minutes total. The reaction was held at a temperature of 220° C. for 3 hours (including the excursion) and was cooled to room temperature then vented. Lustrous iodine crystals were observed on the cooling line and reactor head upon opening the reactor. A dark purple liquid was decanted with some fine grey solids (74.511 g) leaving behind the bulk of dark grey solids. The reaction liquid (40.89 g) was filtered through a 1 micrometer glass microfiber syringe filter to recover 24.827 g of a pink transparent liquid. The filtered liquid was washed with 75 mL 0.5 M HCl(aq) over 3 washes to recover 22.56 g of a burnt orange transparent liquid of approximately 32.9% primary iodide (PI). After purification by distillation and heating of this material at 220° C. for 3 hours, over a 2 hour and 1 hour hold for sampling, led to a recovered yield of 19.71 g that, by $^{19}F$ NMR, contained the primary iodide of Formula II (18.33 g, 32.9 mmol, (26.9% yield)).

Prophetic Example 4: Synthesis of $FSO_2C_2F_4OC(CF_3)=CF_2$

Synthetic example monomer of perfluoroisopropenyl ether ethane sulfonyl fluoride (designated MV(CH3)2S) could be provided by the following reaction scheme:

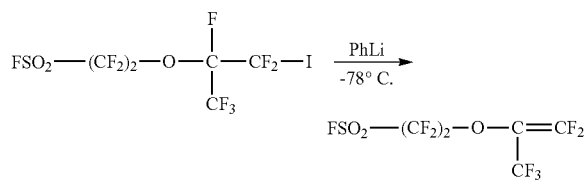

The primary iodide product from Example 3 will be reacted with phenyl lithium (PhLi) as described in Example 2 to form the isopropenyl ether $C_2$ sulfonyl fluoride monomer.

Based on the description of U.S. Pat. No. 7,348,088 and WO 2017/053563, fluoropolymers can be prepared from the monomers described herein.

Prophetic Example 5: TFE/MV(CF$_3$)4S polymer: Poly(tetrafluoroethylene-co-perfluoroisopropenyl ether butane sulfonyl fluoride), $[(CF_2CF_2)p(CF_2C(CF_3)OC_4F_8SO_2F)]q$ Tetrafluoroethylene (TFE) and $CF_2=C(CF_3)OC_4F_8SO_2F$, (MV(CF$_3$)4S), can be copolymerized in a 4 liter reaction vessel by aqueous emulsion polymerization. MV(CF3)4S is made according to Example 2. Polymerization is performed by first making a pre-emulsion of MV(CF3)4S in water with ammonium 4,8-dioxa-3H-perfluorononanoate (ADONA) as an emulsifier by high shear mixing using an Ultraturrax agitator.

A 4-L polymerization kettle equipped with an impeller agitator system (320 rpm) is charged with approximately 2400 g $H_2O$ and 440 g of a 20 weight percent aqueous pre-emulsion of MV(CF3)4S. The kettle is heated to 70° C. and TFE is added to reach 6 bar absolute reaction pressure. The polymerization is initiated by feeding 8 g ammonium persulfate in 100 mL $H_2O$. After a pressure drop, feeding of additional pre-emulsion and gaseous TFE is continued. After about 180 min, the polymerization is stopped. The polymer is coagulated from the reaction mixture and the percent incorporation of MV(CF3)4S monomer is determined by solid state NMR.

Prophetic Example 6: TFE/MV(CF$_3$)2S polymer: Poly(tetrafluoroethylene-co-perfluoroisopropenyl ether ethane sulfonyl fluoride), $[(CF_2CF_2)p(CF_2C(CF_3)OC_2F_4SO_2F)]q$ Tetrafluoroethylene (TFE) and $CF_2=C(CF_3)OC_2F_4SO_2F$, (MV(CF$_3$)2S), are copolymerized in the same manner as Example 5.

What is claimed is:

1. A monomer of the formula:

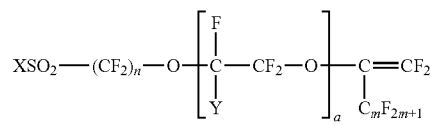

wherein
n ranges from 2 to 8;
Y is F or $C_mF_{2m+1}$;
a is 0, or averages 1 to 2;
m is independently 1, 2, 3, or 4; and
X is F or OH.

2. The monomer of claim 1 wherein m is 1.
3. The monomer of claim 1 wherein a is 0.
4. The monomer of claim 1 wherein n is 2, 3, or 4.
5. The monomer of claim 1 wherein the energy barrier to abstract a fluorine atom by a hydrogen atom (H·) from $C_mF_{2m+1}$ of the ethylenically unsaturated group is greater than the energy barrier to abstract a fluorine atom from $C_mF_{2m+1}$, wherein m is 0.
6. A fluoropolymer comprising polymerized units of the monomer according to claim 1.
7. The fluoropolymer of claim 6, wherein the polymer comprises polymerized units of at least one other ethylenically unsaturated comonomer.
8. The fluoropolymer of claim 7 wherein the polymer comprises polymerized units of at least one other fluorinated ethylenically unsaturated comonomer.
9. The fluoropolymer of claim 8 wherein the other fluorinated ethylenically unsaturated comonomer comprises TFE.
10. A fuel cell membrane comprising a support and a fluoropolymer according to claim 6.
11. The fuel cell membrane of claim 10 wherein the support comprises a nanofiber or expanded PTFE reinforcing material.

12. A membrane electrode assembly comprising the fuel cell membrane of claim 10.

13. A method of making a fluoropolymer comprising:
emulsifying the monomer according to claim 1 in an aqueous liquid;
optionally emulsifying at least one additional ethylenically unsaturated comonomer in the aqueous liquid;
charging a polymerization kettle with the aqueous liquid of emulsified monomer(s); and
heating the aqueous liquid of emulsified monomer under pressure such that the monomers polymerize forming a fluoropolymer.

14. The method of claim 13 further comprises hydrolyzing, ion exchanging with an acid, drying, and dispersing the fluoropolymer in a mixture of alcohol and water.

* * * * *